United States Patent [19]

Jones et al.

[11] Patent Number: 4,620,045

[45] Date of Patent: Oct. 28, 1986

[54] ENEYNOLS FROM ACETYLENES AND PROPARGYLIC ALCOHOLS

[75] Inventors: Giffin D. Jones; Harold E. Doorenbos, both of Midland, Mich.

[73] Assignee: The Dow Chemical Company, Midland, Mich.

[21] Appl. No.: 713,511

[22] Filed: Mar. 19, 1985

[51] Int. Cl.$^4$ .................... C07C 29/32; C07C 33/042
[52] U.S. Cl. .................................. 568/873; 568/813; 568/826
[58] Field of Search ............... 568/873, 813, 826, 828

[56] References Cited

U.S. PATENT DOCUMENTS

| | | | |
|---|---|---|---|
| 2,555,600 | 6/1951 | Newman | 260/615 |
| 2,942,014 | 6/1960 | Cameron | 260/410.6 |
| 3,174,956 | 3/1965 | Luttinger | 260/88.1 |
| 3,940,425 | 2/1976 | Eiter | 568/873 |
| 4,198,533 | 4/1980 | Carney et al. | 568/840 |

FOREIGN PATENT DOCUMENTS 890796  9/1953  Fed. Rep. of Germany ...... 568/873

OTHER PUBLICATIONS

Piganiol, Acetylene Homologs and Derivatives, Mapleton House, Brooklyn, N.Y. (1950), pp. 63–83.
Carlton et al., *J. Chem. Soc., Perkin Transactions*, 1631–1633 (1978).
Copenhaver et al., *Acetylene and Carbon Monoxide Chemistry*, Reinhold, New York, NY (1949), pp. 121–123.
Garwood et al., Chem. Ind., 1684 (1962).
Schmitt and Singer, *J. Organometallic Chem.*, 153, 165–179 (1978) (Netherlands; English translation provided).
Singer & Wilkinson, *J. Chem. Soc. Part A*, 849–853 (1968).
Crombie et al., *J. Chem. Soc.*, 126–135 (1956).
Gverdtsiteli, CA 42:6738i (1948).
Reppe, CA 40:2685 (1946).
Yoshikawa et al., Makromol. Chem., 178, 1077–1087 (1977).

*Primary Examiner*—J. E. Evans
*Attorney, Agent, or Firm*—Christopher J. Rudy; Norman L. Sims

[57] ABSTRACT

Eneynols are prepared from terminal acetylenes and propargylic alcohols using a $Cu^+$, $Ag^+$ and/or $Au^+$ halide catalyst.

30 Claims, No Drawings

ENEYNOLS FROM ACETYLENES AND PROPARGYLIC ALCOHOLS

BACKGROUND OF THE INVENTION

The invention is a process for coupling terminal acetylenes with propargylic alcohols to prepare eneynols.

The coupling of acetylenes is well-known. In the presence of alcohols, acetylenes and acetylenic alcohols are known to yield ethers, acetals, ketals and the like. In the case of alcohols of more than three carbons and simple aliphatic acetylenes, polymerization into nondistilled resins comlicates the often violent reaction. See e.g., Piganiol, *Acetylene Homologs and Derivatives*, Mapleton House, Brooklyn, NY (1950).

The dimerization of propargyl alcohol is known to give 2,4-hexadiyne-1,6-diol using cuprous chloride catalysts in the presence of oxygen. See also, Garwood et al., *Chem. Ind.* (1962) at p. 1684.

The coupling of 3,4-dimethylpent-1-yn-3-ol and phenylacetylene in the presence of tris(triphenylphosphine)rhodium (I) chloride catalyst is known to yield a mixture of products which includes homodimers and about 12 percent 2-phenyl-5,6-dimethyl-pent-1-ene-3-yn-5-ol and about 19 percent 1-phenyl-5,6-dimethyl-pent-1-ene-3-yn-5-ol. See e.g., Schmitt and Singer, *J. Organometallic Chem.* 153, 165–179 (1978) (Netherlands).

The preparation of certain eneynols otherwise generally proceeds by the reaction of Grignard reagents, see e.g., Crombie et al., *J. Chem. Soc.*, 126 (1956), which are not suited commercially for larger scale production. Or, certain eneynols have been prepared by condensing formaldehyde with 1-buten-3-ynyl compounds, notably 1-buten-3-yne, also yielding significant amounts of tars. See. e.g., Gverdtsiteli, CA 42:6738 (1948).

What is needed is a process for preparing eneynols which is controllable and efficient both economically, especially in larger scale commercial applications, and materially, especially in reduction of unwanted tars and other polymerization by-products.

SUMMARY OF THE INVENTION

The invention is a process to prepare eneynols comprising contacting a terminal acetylene with a propargylic alcohol in the presence of a catalyst comprising a metallic halide of the group Cu(I), Ag(I), Au(I) or combination thereof under conditions such that an eneynol is produced.

The products are useful as solvents, lubricants, combustibles, and as intermediates in other organic syntheses, such as in halogen addition.

The invention is a controllable process, and it is economically and materially efficient. The reactants are readily available and relatively inexpensive to obtain, and the process produces eneynols without producing excess unwanted by-products, such as tars and homodimers.

DETAILED DESCRIPTION OF THE INVENTION

Terminal acetylenes are hydrocarbons which contain at least one ethynyl group. Preferably, terminal acetylenes are otherwise saturated. For example, the compound acetylene, phenylacetylene and 1-heptyne are terminal acetylenes.

In all terminal acetylenes it is another preference that the terminal acetylenes are of the formula $R-C\equiv C-H)_x$ wherein independently each occurrence R is hydrogen or carbon-containing group inclusively from one to about 20 carbons which may otherwise contain only hydrogen. The positive integer x is from one to 2m plus 2 wherein m is the number of carbons in R. More preferred terminal acetylenes are those wherein R is independently each occurrence hydrogen or said carbon containing group inclusively of from one to about ten, especially of from one to 6, carbons.

Examples of said carbon-containing groups are methyl, methylene, neocarbyl (i.e. herein a carbon to which four groups are to be attached), ethyl, propyl, allyl, cyclohexyl, phenyl, hydrocarbyl-substituted phenyl (i.e. herein a phenyl group which has substituted thereon for hydrogen at least one hydrocarbon radical such as methyl, ethyl, allyl, 2-butynyl, decyl and the like, or combination of said radicals, having no more carbon therein than each preference allows) eicosyl, 2-methyleicosyl and the like.

In all terminal acetylenes, it is another preference that no more than one ethynyl group is directly bonded to any one atom, and it is more preferred that this atom is hydrogen or the carbon of a phenyl, hydrocarbyl-substituted phenyl or a methylene group.

In all terminal acetylenes, it is another preference that there be present only one or two, more preferably one, ethynyl group(s). Diynes of lower carbon number and/or where the triple bonds are conjugated or close are relatively unstable. Desirable terminal acetylenes include acetylenes from the compound acetylene through cyclohexylacetylene and phenylacetylene. The most desirable terminal acetylene is the compound acetylene.

Propargylic alcohols are compounds which contain at least one ethynyl group and at least one hydroxyl group, otherwise may contain only hydrogen, and which contain at least one propargylic carbon. A propargylic carbon herein is a carbon to which at least one ethynyl group and hydroxyl group are directly bonded. A preferred propargylic carbon has only one ethynyl and one hydroxyl group directly bonded to it. Preferably, propargylic alcohols are otherwise saturated. For example, the compound propargyl alcohol, 1,10-undecadiyn-3-ol and 1-heptyn-3-ol are propargylic alcohols.

In all propargylic alcohols it is another preference that the propargylic alcohols are of the formula $(H-C\equiv C-)_y R'-OH)_z$ wherein $R'$ is independently each occurrence a carbon-containing group inclusively from one to about 20 carbons, which may otherwise contain only hydrogen, and have at least one propargylic carbon. The positive integers y and z are each from one to 2n plus 1, and the maximum value of y plus z is 2n plus 2, wherein n is the number of carbons in $R'$. Even more preferred propargylic alcohols are those wherein $R'$ is independently each occurrence said carbon-containing group inclusively of from one to about 10, most preferably of from one to 7, carbons.

In all propargylic alcohols, it is another preference that each propargylic carbon is a preferred propargylic carbon, and it is even more preferred therein that there is independently each occurrence no other additional ethynyl group(s) or no other additional hydroxy group(s) present. It is most preferred therein that no other additional ethynyl and hydroxy groups are present.

In all propargylic alcohols, it is another preference that no more than one propargylic carbon is bonded to any one atom. It is more preferred therein that those two atoms bonded to the propargylic carbon are independently each occurrence hydrogen(s) and/or the carbon(s) of a (a) phenyl, hydrocarbyl-substituted phenyl, methyl or methylene group(s), most preferably hydrogen(s) and at most the carbon of one phenyl, methyl or methylene group if any.

In all propargylic alcohols, it is another preference that there be present one or two, more preferably one, propargylic carbon(s). The most desirable propargylic alcohol is the compound propargyl alcohol.

The catalyst comprises a catalytic metallic halide of the group Cu(I), Ag(I), Au(I) or combinations thereof. The Roman numerals in the parentheses indicate the positive oxidation state of the metallic component of the halide. Halides herein are chloride, bromide and iodide, with the chloride preferred. Also, cuprous halides are preferred due to their inexpensiveness and potential water-solubility. Cuprous chloride is more preferred. Another preferred group is the group of argentous and aurous halides.

In general, the catalysts of the invention are prepared in a manner like the known cuprous halide catalysts. See e.g., Piganiol, supra at pp. 63–83 (which pages are herein incorporated by reference); especially see pp. 72–77.

Water is preferentially present in the catalyst. The lower limits of the mole ratio of the number of moles of water to the number of moles of catalytic metallic halide present are preferably about one, more preferably about two and most preferably about five. Equivalent upper limits are preferably about 100, more preferably about 20 and most preferably about ten.

In addition, a protic acid is preferentially present in the catalyst. The acid is more preferably a hydrogen halide mineral acid, and most preferably a hydrogen halide mineral acid wherein the halide of the mineral acid and the catalyst metal halide are the same. The lower limits of the mole ratio of acidic hydrogens in the acid to catalytic metallic halide present before any acid addition are preferably about 0.001, more preferably about 0.01 and most preferably 0.02. Equivalent upper limits are preferably about one, more preferably about 0.1 and most preferably about 0.05.

In addition, it is preferred that an elemental metal of the group Cu, Ag, Au or combination thereof is present in the catalyst. More preferably the elemental metal present corresponds to the metallic portion of the catalytic metallic halide present. The lower limits of the mole ratio of elemental metal to catalytic metallic halide present before any acid addition are preferably about 0.1 and more preferably about 0.5. Equivalent upper limits are preferably about two and more preferably about one.

In addition, it is preferred that a nitrogen-containing coordination compound such as ammonia, primary, secondary, tertiary amines, polyamines, pyridinols, the like and mixtures thereof, more preferably their halide salts, most preferably an ammonium halide, primary or secondary alkylamino or (poly)amino halide or combination thereof, most preferably wherein the halide of these more preferred nitrogen-containing halides and the catalyst metal halide are the same, be present in the catalyst. The lower limits of the mole ratio of nitrogens available for coordination to the metallic portion of the catalyst (for example, one mole of ethylenediamine has two moles of nitrogen available for such coordination) to catalytic metallic halide present before any acid addition are preferably about 0.1 and more preferably about one. Equivalent upper limits are preferably about 12 and more preferably about five.

One coupling produces an eneynol, which comprises a compound with at least one eneynolic bond between the remnants of the terminal acetylene and the propargylic alcohol. An eneynolic bond had three general aspects. The first is directed conjugation of the eneyne-bond such that there extends from the (formerly) propargylic carbon a single- to triple- to single- to double- to single-bond system. The second is that the terminal acetylene remnant is directly bonded by a single bond to a doubly-bonded carbon of the eneynolic bond. The third is that the propargylic alcohol remnant retains at least one hydroxyl group.

A remnant is that portion of a reactant which does not participate in eneynolic bond forming and is otherwise recognizable as being derived from the reactants which participate in eneynolic bond forming. Preferably, at least one remnant retains at least all of the carbons from which it is derived, more preferably retaining all the atoms with the same structure, other than the carbon in the eneynolic bond(s) formed. Most preferably, each remnant interconnected by an eneynolic bond retains all of the elements from which each is derived, especially preferably each with the same structure, other than those involved in the eneynolic bond. For example, the remnants of the coupled compounds acetylene and propargyl alcohol in 4-penten-2-yn-1-ol are respectively hydrogen and hydroxymethyl, satisfying the criteria of the especially preferred embodiment.

In general, one coupling produces an eneynol of the formula Q—CH=CQ—C≡C—Q'—OH)$_{z-a}$ wherein independently each occurrence Q is each occurrence a remnant of the coupled terminal acetylene or hydrogen. Both Q's cannot be each carbon-containing. It is a preference that Q be hydrogen in the carbon closest to the triple bond of the eneynolic bond;

Q'—OH)$_{z-a}$ is a remnant of the coupled propargylic alcohol with z as hereinbefore defined for R'; and "a" is a natural number of value $0 \leq a \leq z$ minus 1.

Multiple eneynolic, and mixed eneynolic/other bonds are possible.

The reaction is carried out in a suitable vessel, which is preferably closed. The reactants may be combined neat or in the presence of an inert solvent such as gaseous argon, liquid or gas alkanes or an alkyl alcohol. Maximum contact is achieved by stirring, flow methods, high temperature and/or pressure diffusion and other suitable known means.

Temperatures are such that the eneynol is produced. Preferred lower limits of temperature are about 20° C., due to generally slower reaction rates below this lower limit. More preferable lower limits are about 60° C., most preferably about 75° C. Preferred upper limits of temperature are about 100° C., due to increasing decomposition above this upper limit. More preferable upper limits are about 90° C., most preferably about 85° C.

Pressures are such that the eneynol is produced. Lower limits of pressure are preferably about ambient atmospheric pressure, more preferably about 100 psig (i.e. about 6.8 atmospheres; gauge pressure of about 690 kPa) and most preferably about 150 psig (i.e. about 10.2 atmospheres; gauge pressure of about 1040 kPa). Upper limits of pressure are preferably about 3000 psig (i.e. about 200 atmospheres; gauge pressure of about 20700 kPa), more preferably about 500 psig (i.e. about 34 atmospheres; gauge pressure of about 3450 kPa) and most preferably about 400 psig (i.e., about 27.2 atmospheres; gauge pressure of about 2800 kPa). These preferred pressure limits are due to generally slower reaction rates at the lower limits and the increasing explosiveness of the highly pressurized acetylenes and acetylides at successively higher limits.

The terminal acetylene and propargylic alcohol are present in any ratio such that an eneynol is produced. Preferably, the lower limits of mole ratio of terminal acetylene to propargylic alcohol present as reactants based on the number of moles of ethynyl groups on the terminal acetylene(s) and propargylic alcohol(s) are about 0.01, more preferably about 0.1. Equivalent upper limits are preferably about 1000 and more preferably about one hundred. An excess of the terminal acetylene based on number of ethynyl groups present is most preferred when the terminal acetylene is in the gaseous state and the propargylic alcohol is in a more dense state, such as a liquid. The excess has an especially preferred mole ratio at the lower limit of about five. An equivalent especially preferred upper limit is about twenty-five. If the terminal acetylene is phenylacetylene it is also most preferred that a nearly stoichiometric amount of it and the propargylic alcohol, based on number of ethynyl groups, be present.

The catalyst is present in any amount that catalyzes the reaction. Preferable lower limits of mass of catalyst used in relation to the mass of limiting reagent plus mass of catalyst present are about $1 \times 10^{-3}$ percent and more preferably about 1 percent. Equivalent preferable upper limits are about 99 percent and more preferably about 80 percent.

The reaction is carried out until the desired level of completion is accomplished. Preferably, for complete formation of eneynolic bonds, times of about 10 hours or more are advantageous. Times in excess of about 100 hours may cause decomposition and allow unwanted excess polymerization. Completion and identification of products can be easily checked by methods known in the art. The products may be separated from the reaction mixture by methods known in the art such as extraction, chromatography, evaporation of solvent, vacuum distillation, freezing, centrifugation, filtration and the like, or may be used as an intermediate product without such purification, where advantageous.

Preferably eneynols are produced in major amounts, more preferably above about 20 percent, most preferably above about 33 percent, especially above about 50 percent, of theoretical. Other preferences in each of the foregoing production amounts are wherein the eneynols are of the formula Q—CH=CH—C≡C—Q'—OH)$_{z-a}$.

SPECIFIC EMBODIMENTS

The following example is illustrative of the invention:

EXAMPLE

Preparation of 4-Penten-2-yn-1-ol

The catalyst is prepared by heating overnight at 65° C. in a closed 75-ml stainless steel Hoke cylinder the following mixture: cuprous chloride (3.3 g), ammonium chloride (2.4 g), copper dust (0.15 g), water (4.17 g), and concentrated hydrochloric acid (0.075 g).

Propargyl alcohol (3 g) is added to the catalyst, the cylinder is pressurized to 200 psig (about 13.6 atmospheres; gauge pressure of about 1380 kPa) with acetylene, and the mixture is placed on a shaker at 80° C.-85° C. for 10 hours. The product is filtered, and the filtrate is extracted with methylene chloride. The methylene chloride is distilled, leaving the product in a residue.

We claim:

1. A process to prepare eneynols comprising contacting a terminal acetylene with a propargylic alcohol in the presence of a catalyst comprising a metallic halide of $Cu^+$, $Ag^+$, $Au^+$ or combination thereof under conditions such that an eneynol is produced, wherein
    the terminal acetylene is a hydrocarbon which contains at least one ethynyl group;
    the propargylic alcohol is a hydroxyl-substituted hydrocarbon which contains at least one ethynyl group and contains at least one propargylic carbon, said propargylic carbon to which at least one ethynyl group and at least on hydroxyl group are directly bonded, and
    the eneynol is a compound with at least one eneynolic bond between remnants of the terminal acetylene and the propargylic alcohol.

2. The process of claim 1 conducted in an inert solvent.

3. The process of claim 1 conducted at a temperature from about 20° C. to about 100° C.

4. The process of claim 3 wherein the terminal acetylene is of the formula R—C≡C—H)$_x$ wherein R is hydrogen or a carbon-containing group inclusively from one to about 20 carbons which may otherwise contain only hydrogen, x is an integer from 1 to 2m+2 wherein m is the number of carbons in R, and the propargylic alcohol is of the formula (H—C≡C—$_y$R'—OH)$_z$ wherein R' is a carbon-containing group inclusively from one to about 20 carbons which may otherwise contain only hydrogen, y and z are each an integer from 1 to 2n+1 with the maximum value of y plus z equal to 2n+2 wherein n is the number of carbons in R'.

5. The process of claim 4 wherein independently each occurrence R is hydrogen or a carbon-containing group inclusively of from one to about 20 carbons and independently each occurrence x, y and z have values of one or two.

6. The process of claim 5 wherein independently each occurrence R is hydrogen or a carbon-containing group inclusively of from one to about 10 carbons and each propargylic carbon is bonded to the carbon of a phenyl, hydrocarbyl-substituted phenyl, methyl or methylene group and hydrogen or to two hydrogens.

7. The process of claim 6 conducted at a pressure of from about 100 psig to about 500 psig.

8. The process of claim 7 wherein the catalyst comprises a cuprous halide.

9. The process of claim 8 wherein the catalyst additionally contains water.

10. The process of claim 9 wherein the catalyst additionally contains a protic acid.

11. The process of claim 10 wherein the acid is a hydrogen halide mineral acid.

12. The process of claim 11 wherein the catalyst additionally contains elemental copper.

13. The process of claim 12 wherein the catalyst additionally contains a nitrogen-containing coordination compound.

14. The process of claim 13 wherein the nitrogen-containing coordination compound is an ammonium halide, primary or secondary alkylamino or (poly)amino halide or combination thereof.

15. The process of claim 13 wherein x, y and z have values of one.

16. The process of claim 15 wherein independently each occurrence R' is inclusively from one to about 10 carbons.

17. The process of claim 16 wherein the cuprous halide is cuprous chloride.

18. The process of claim 17 wherein the terminal acetylene is the compound acetylene.

19. The process of claim 18 wherein the propargylic alcohol is the compound propargyl alcohol.

20. The process of claim 19 conducted at a temperature from about 60° to about 90° C.

21. The process of claim 1 wherein the terminal acetylene is the compound acetylene and the propargylic alcohol is the compound propargyl alcohol.

22. The process of claim 8 wherein the terminal acetylene is the compound acetylene and the propargylic alcohol is the compound propargyl alcohol.

23. The process of claim 1 wherein the terminal acetylene and the propargylic alcohol are present as reactants in a terminal acetylene:propargylic alcohol ratio based on number of moles of ethynyl groups on the terminal acetylene and propargylic alcohol from about 0.01:1 to about 1000:1.

24. The process of claim 9 wherein the water is present in a water:cuprous halide molar ratio of from about 2:1 to about 20:1.

25. The process of claim 24 wherein the catalyst additionally contains a protic acid present in an acidic hydrogen:cuprous halide molar ratio of from about 0.01:1 to about 0.1:1.

26. The process of claim 25 wherein the acid is a hydrogen halide mineral acid.

27. The process of claim 26 wherein the catalyst additionally contains elemental copper present in a copper:cuprous halide molar ratio, before acid addition, of from about 0.1:1 to about 2:1.

28. The process of claim 27 wherein the catalyst additionally contains a nitrogen-containing coordination compound present in a nitrogen available for coordination:cuprous halide molar ratio, before acid addition, of from about 1:1 to about 5:1.

29. The process of claim 28 wherein the nitrogen-containing coordination compound is an ammonium halide, primary or secondary alkylamino or (poly)amino halide or combination thereof.

30. The process of claim 29 wherein the cuprous halide is cuprous chloride; the acid is hydrochloric acid; the nitrogen-containing coordination compound is ammonium chloride; the terminal acetylene is the compound acetylene; the propargylic alcohol is propargyl alcohol; and the eneynol is 4-penten-2-yn-1-ol.

* * * * *